United States Patent [19]

Strickler et al.

[11] Patent Number: 5,254,707
[45] Date of Patent: Oct. 19, 1993

[54] PREPARATION OF CYCLOPENTADIENE DERIVATIVES

[75] Inventors: Jamie R. Strickler; John M. Power; Meng-Sheng Ao, all of Baton Rouge, La.

[73] Assignee: Ethyl Corporation, Richmond, Va.

[21] Appl. No.: 986,197

[22] Filed: Dec. 7, 1992

[51] Int. Cl.$^5$ .................... C07C 22/00; C07C 83/00
[52] U.S. Cl. .................... 556/413; 556/81; 556/87; 556/430; 564/305; 564/395; 564/428; 564/445; 564/454; 564/455; 564/460
[58] Field of Search ............. 556/413, 430, 435, 81, 556/87; 564/305, 395, 428, 426, 445, 450, 454, 455, 460

[56] References Cited

U.S. PATENT DOCUMENTS

| | | | |
|---|---|---|---|
| 4,293,687 | 10/1981 | Weissel et al. | 564/395 X |
| 4,673,759 | 6/1987 | Dalcanale | 564/455 X |
| 4,999,443 | 3/1991 | Bertleff et al. | 556/28 X |
| 5,189,192 | 2/1993 | LaPointe et al. | 556/81 X |

FOREIGN PATENT DOCUMENTS 0416815 3/1991 European Pat. Off.

*Primary Examiner*—Arthur C. Prescott
*Attorney, Agent, or Firm*—David M. Bunnell

[57] ABSTRACT

The process for preparing a compound of the formula:

Cp'YNHR wherein: Cp' is a cyclopentadienyl or a substituted cyclopentadienyl group, Y is a covalent bridging group which contains one or more group 14 elements, and R is a $C_1$ to $C_{20}$ hydrocarbyl or substituted hydrocarbyl group, the process comprising reacting a ligand of the formula Cp'YX, wherein Cp' and Y are as defined above and X is halogen, with a substantially equimolar amount of a primary amine of the formula $NH_2R$, wherein R is as defined above, in an inert solvent in the presence of a HX scavenger at an elevated temperature of at least about 35° C., so as to form said compound.

13 Claims, No Drawings

PREPARATION OF CYCLOPENTADIENE DERIVATIVES

This invention relates generally to the preparation of cyclopentadienyl derivatives and more specifically to the preparation of secondary amine derivatives of compounds containing a cyclopentadienyl moiety, which derivatives are useful ligands for forming Ziegler-Natta polymerization catalysts.

It is known to prepare compounds of the formula Cp'YNHR, wherein Cp' is a cyclopentadienyl or a substituted cyclopentadienyl group, Y is a covalent bridging group which contains one or more group 14 elements and, preferably, silicon, germanium and/or carbon, and R is $C_1$ to $C_{20}$ hydrocarbyl or substituted hydrocarbyl, by reacting one mole of a ligand of the formula Cp'YX, wherein X is halogen and Cp' and Y are as defined above, with two moles of an amine of the formula $NH_2R$, wherein R is as defined above, according to the reaction:

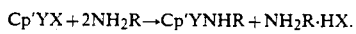

Cp'YX + 2NH$_2$R → Cp'YNHR + NH$_2$R·HX.

The amine hydrohalide salt, usually the HCl salt, precipitates from the reaction mixture. An excess, or about 1.5 to 2 or more equivalents (3 to 4 moles of amine per mole Cp' ligand) of amine reactant is used in order to provide reasonable reaction rates and to compensate for the reaction of the amine reactant with HCl, which reaction can occur even when a HCl scavenger such as a tertiary amine is used in the reaction. When the amine reactant is a lower boiling amine such as a methyl-, ethyl-, propyl- or butylamine, the excess amine can be readily separated from the product ligand by distillation. However, when amines which contain five or more carbon atoms are reacted and especially amines having from about 10 to 20 carbon atoms, the separation of unreacted excess amine becomes increasingly difficult due to a smaller boiling point difference between the amine and the product. The presence of such unreacted amine leads to the formation of undesirable impurities, such as amine-metal complexes, when the ligand is reacted with a metal compound to form a metallocene catalyst.

We have now discovered an improved process for forming the amine ligands which uses less than equivalent amounts, and preferably nearly equimolar amounts, of amine reactant and still provides good yields of product at reasonable reaction rates.

In accordance with this invention there is provided a process for preparing a compound of the formula:

Cp'YNHR wherein: Cp' is a cyclopentadienyl or a substituted cyclopentadienyl group, Y is a covalent bridging group which contains one or more group 14 elements, and R is a $C_1$ to $C_{20}$ hydrocarbyl or substituted hydrocarbyl group, the process comprising reacting a ligand of the formula Cp'YX, wherein Cp' and Y are as defined above and X is halogen, with from about 0.9 to 1.1 mole per mole of said ligand of a primary amine of the formula $NH_2R$, wherein R is as defined above, in an inert solvent in the presence of a hydrogen halide scavenger at an elevated temperature of at least about 35° C. so as to form said compound.

Preferred cyclopentadienyl groups Cp' can be represented by the formula:

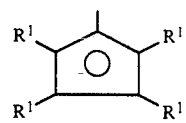

wherein $R^1$ each occurrence is hydrogen or a moiety selected from the group consisting of silyl, germyl, hydrocarbyl, substituted hydrocarbyl and combinations thereof having up to 20 (preferably 1 to 10) carbon, germanium and/or silicon atoms, and two $R^1$ substituents can together form a ring fused to the cyclopentadienyl moiety. Non-limiting examples of fused ring cyclopentadienyl derivatives include indenyl, tetrahydroindenyl, fluorenyl, octahydrofluorenyl, and the like, which rings can be further substituted. Non-limiting examples of other suitable $R^1$ groups, which $R^1$ groups can be the same or different and can be substituted for 1 to 4 hydrogen atoms on the cyclopentadienyl ring, include straight or branched chain hydrocarbyl radicals, including halogen and alkoxy substituted hydrocarbyl radicals, cyclic hydrocarbyl radicals, including alkyl, alkoxy and halogen, substituted cyclic hydrocarbyl radicals, aromatic hydrocarbyl radicals including alkyl, alkoxy and halogen substituted aromatic radicals, and organometalloid radicals of silicon and germanium. Specific non-limiting examples of preferred $R^1$ moieties include methyl, ethyl, propyl, butyl, pentyl, hexyl, (including isomers), norbornyl, benzyl, phenyl, trimethylsilyl, triethylsilyl, ethyldimethylsilyl, methyldiethylsilyl, phenyldimethylsilyl, methyldiphenylsilyl, triphenylsilyl, triphenylgermyl, trimethylgermyl, methylmethoxy, methylethoxy, and the like.

Preferred bridging groups, Y, contain 1–4 atoms in the bridge, which atoms are selected from Group 14 elements of the Periodic Table and especially silicon, germanium and carbon. Non-limiting examples of bridging groups are $SiR_2''$, $CR_2''$, $SiR_2''SiR_2''$, $CR_2''CP_2''$, $CR_2''SiCR_2''$, $CR''=CR''$, $GeR_2''$ wherein R'' each occurrence is hydrogen or a moiety selected from silyl, germanyl, hydrocarbyl, substituted hydrocarbyl (e.g. aralkyl, alkaryl, haloalkaryl and haloaralkyl) and combinations thereof having up to 20 non-hydrogen atoms. Specific non-limiting examples of preferred R'' moieties include methyl, ethyl, propyl, butyl, pentyl, hexyl (including isomers), trimethylsilyl, triethylsilyl, ethyldimethylsilyl, methyldiethylsilyl, phenyldimethylsilyl, methyldiphenylsilyl, triphenylsilyl, triphenylgermyl and the like. The halogen, X, on the bridging group can be chlorine, bromine or iodine and, preferably, is chlorine.

Preferred primary amine reactants have the formula $NH_2R$, wherein R is a $C_1$ to $C_{20}$ straight or branched chain hydrocarbyl or substituted hydrocarbyl radical, including halogen and alkoxy substituted hydrocarbyl radicals, cyclic hydrocarbyl radicals, including alkyl, alkoxy and halogen substituted cyclic hydrocarbyl radicals, aromatic hydrocarbyl radicals including alkyl, alkoxy and halogen substituted aromatic hydrocarbyl radicals. Specific non-limiting examples of preferred R moieties include pentyl, hexyl, heptyl, octyl, nonyl, decyl, dodecyl, tetradecyl, hexadecyl, octadecyl, and the like.

Preferred hydrogen halide scavengers are tertiary amines. Specific non-limiting examples of preferred tertiary amines include trimethylamine, triethylamine, tributylamine, N-methylpyrrolidine, ethyldimethylamine, pyridine, and the like.

The Cp'YX reactant can be prepared by known procedures such as by reacting a deprotonated Cp', e.g. a sodium or lithium Cp' salt, with $YX_2$ in an ether solvent such as THF or diethyl ether.

The Cp'YX reactant and the primary amine reactant are reacted in proportions of from about 0.9 to 1.1 moles of amine reactant per mole of Cp'YX reactant.

The HCl scavenger is preferably used in excess such as from about 1.1 to 25 moles per mole of Cp'YX reactant.

The reaction is carried out in an inert organic solvent and preferably in from about 50 to 90 weight percent solvent, based on the total weight of reaction mixture. Examples of preferred solvents include ethers such as diethyl ether, tetrahydrofuran (THF), glyme, diglyme, etc., and the like and aliphatic or aromatic hydrocarbons such as hexane, heptane, cyclohexane, toluene and the like.

The reaction temperature should be at least about 35° C. and preferably from about 40° to 100° C. and more preferably for about 50° C. to 70° C. The elevated reaction temperature not only drives the reaction to completion, but gives a fast reaction which is very selective in that very little amine reactant is lost due to HX salt formation. This permits about equimolar portions of amine reactant to Cp'YX reactant to be used while still achieving high yields. Because about equimolar portions can be used, very little if any unreacted amine remains in the product mixture. Preferably, a mixture of solvent, cyclopentadienyl reactant and scavenger is heated to reaction temperature prior to adding the amine reactant such that the initial contacting of the reactants takes place at elevated temperatures. Also, the amine reactant is added slowly over a period of time, for example, from about ½ to 2 hours or more in order to obtain a selective reaction with the Cp'YX reactant and avoid primary amine-HX salt formation. During the reaction, the HX salt of the scavenger precipitates from the reaction mixture and is removed such as by filtration to yield a product solution from which the solvent can be removed by conventional techniques to provide a product which is substantially free of unreacted reactant amine. The process thus avoids the presence of unreacted primary amines and especially higher boiling amines such as $C_5$ to $C_{20}$ amines, which would be difficult to remove from the reaction mixture and would produce undesirable amine-metal complexes when the product is reacted with a metal salt to form a metallocene catalyst. Such amine-metal complex impurities can interfere with the performance of the catalyst when used to polymerize olefins.

The invention is further illustrated by, but is not intended to be limited to, the following examples.

EXAMPLE 1

In a 100 mL Schlenk flask were placed 2.01 grams of $(C_5Me_4H)SiMe_2Cl$ (0.00936 mol), 16 mL of THF, and 2.00 grams of triethylamine (0.0198 mol). This solution was warmed to 50° C. A solution of 1.81 grams (0.00987 mol) of cyclododecylamine in 14 mL of THF was added to the silane/$Et_3N$ solution over 90 minutes. The solution clouded with precipitates as cyclododecylamine was added. At the end of the addition, the solution was thick with solids. The reaction was held at 50° C. for another two hours. The reaction was cooled to room temperature and the white solids of $Et_3N \cdot HCl$ were filtered to yield a clear, pale yellow solution. The solids were washed and dried in vacuo. The yield of solids was 1.24 grams or 96%. $^1H$ NMR ($CDCl_3$ and $D_2O$) showed only $Et_3N \cdot HCl$ and no $C_{12}H_{23}NH_2 \cdot HCl$. The filtrate was concentrated and filtered to yield 2.98 grams (88%) of a pale yellow liquid product which was identified as $(C_5Me_4H)SiMe_2(NHC_{12}H_{23})$ by $^1H$ NMR ($C_6D_6$). The lack of primary amine salt by-product demonstrates a surprising selectivity which allows about equimolar amounts of amine reactant to be used in order to minimize the amount of unreacted amine and still provide high yields of product.

COMPARISON 1

A solution of 9.4 grams (0.051 mol) of cyclododecylamine in 50 mL of cyclohexane was added to a solution of $(C_5Me_4H)SiMe_2Cl$ (5.5 grams, 0.026 mol) in 200 mL of cyclohexane. A white solid began to form immediately. After 10 minutes the reaction mixture had become quite thick with $C_{12}H_{23}NH_2 \cdot HCl$. The slurry was stirred overnight. The following day, the mixture was filtered and the solids were washed with ether. The filtrate clouded immediately and solids continued to form. Starting material was detected by GC. The reaction was allowed to stir overnight again. After stirring a second night, the reaction had again become quite thick with gelatinous solids. GC showed 10% of $(C_5Me_4H)SiMe_2Cl$ is still present. After filtering a second time, the reaction was concentrated and stirred a third night. The next day most of the starting material was converted to product. This illustrates that at ambient temperatures using a stoichiometric amount of amine and without a scavenger the reaction was very slow.

COMPARISON 2

In a 100 mL flask were placed 2.00 grams of $(C_5Me_4H)SiMe_2Cl$ (0.00931 mol), 20 mL of $Et_2O$, and 1.30 grams of triethylamine ($Et_3N$, 0.0128 mol). A solution of 1.75 g (0.00954 mol) of cyclododecylamine in 15 mL of $Et_2O$ was added to the solution of silane over 15 minutes. The solution clouded with precipitate. The solution slowly became thick with solids. The reaction was stirred overnight. The next morning the reaction was filtered on a course frit. The filtrate again clouded with gelatinous precipitate. It was obvious that the reaction at ambient temperatures using equimolar amounts of reactants and a scavenger was much slower than in Example 1 and would be uneconomical.

COMPARISON 3

An amount of 0.02 mol of $(C_5Me_4H)SiMe_2Cl$ in THF was treated with 0.03 mol of triethylamine at 5° C. A solution of 0.03 mole of cyclododecylamine in THF was then added and the reaction was allowed to warm up to room temperature. After 1 hour at room temperature, the mixture was heated up to 65° C. After 0.5 hour, GC showed most of the $(C_5Me_4H)SiMe_2Cl$ had reacted to form $(C_5Me_4H)SiMe_2(NHC_{12}H_{23})$. After the mixture was cooled to room temperature, the white solid precipitate was filtered off. The precipitates were neutralized with base and the organic portion was identified to be a mixture of triethylamine and cyclododecylamine. This shows that during the reaction, the cyclododecylamine as well as the triethylamine had reacted with the HCl such that the two amines would be expected to compete for the HCl generated in the reaction. Therefore, in order to obtain a highly selective reaction (Et$_3$N·HCl only), the cyclododecylamine (the primary amine) should be added slowly to a heated solution of Cp'SiMe$_2$X and Et$_2$N.

What is claimed is:

1. A process for preparing a compound of the formula:

Cp'YNHR wherein: Cp' is a cyclopentadienyl or a substituted cyclopentadienyl group, Y is a covalent bridging group which contains one or more group 14 elements, and R is a C$_1$ to C$_{20}$ hydrocarbyl or substituted hydrocarbyl group; said process comprising reacting a ligand of the formula:

Cp'YX wherein Cp' and Y are as defined above and X is halogen; with from about 0.9 to 1.1 mol per mole of said ligand of a primary amine of the formula:

NH$_2$ wherein R is as defined above; in an inert solvent in the presence of a HX scavenger at an elevated temperature of at least about 35° C. so as to form said compound.

2. The process of claim 1 wherein said HX scavenger is a tertiary amine which is present in an amount of from about 1.1 to 25 moles per mole of ligand.

3. The process of claim 2 wherein R is a C$_5$ to C$_{20}$ hydrocarbyl or substituted hydrocarbyl group.

4. The process of claim 2 wherein R is a C$_{10}$ to C$_{20}$ hydrocarbyl group.

5. The process of claim 2 wherein said temperature is from about 40° to 100° C.

6. The process of claim 2 wherein said temperature om about 50° to 70° C.

7. The process of claim 1 wherein X is chloride.

8. The process of claim 2 wherein X is chloride.

9. The process of claim 2 wherein said solvent is present in an amount of from about 50 to 90 weight percent based on the total weight of reaction mixture.

10. The process of claim 2 wherein R is a C$_{10}$ to C$_{20}$ hydrocarbyl or substituted hydrocarbyl group, said temperature is from about 4° to 100° C., and X is chloride.

11. The process of claim 10 wherein said temperature if from about 50° to 70° C.

12. The process of claim 2 wherein CpYX is C$_5$Me$_4$H)SiMe$_2$Cl, NH$_2$R is cyclododecylamine, and said product is C$_5$MeH)SiMe$_2$(NHC$_{12}$H$_{23}$).

13. The process of claim 12 wherein said scavenger is triethylamine.

* * * * *

UNITED STATES PATENT AND TRADEMARK OFFICE
CERTIFICATE OF CORRECTION

PATENT NO. : 5,254,707  
DATED : October 19, 1993  
INVENTOR(S) : Jamie R. Strickler et al Page 1 of 2

It is certified that error appears in the above-indentified patent and that said Letters Patent is hereby corrected as shown below:

Column 5:

Claim 1, line 30, reads "$NH_2$", but should read -- $NH_2R$ --.

Column 6:

Claim 6, lines 13-14, reads "...said temperature om about...", but should read -- ...said temperature is from about... --.

Claim 10, line 22, reads "...is from about 4° to 100°C....", but should read -- ...is from about 40° to 100°C.... --.

Claim 12, line 27, reads "$C_5Me_4H)SiMe_2Cl,...$", but should read -- $(C_5Me_4H)SiMe_2Cl,...$ --.

UNITED STATES PATENT AND TRADEMARK OFFICE
CERTIFICATE OF CORRECTION

PATENT NO. : 5,254,707
DATED : October 19, 1993
INVENTOR(S) : Jamie R. Strickler et al It is certified that error appears in the above-indentified patent and that said Letters Patent is hereby corrected as shown below:

Column 6:
Claim 12, line 28, reads "...$C_5MeH)SiMe_2(NHC_{12}H_{23})$.", but should read --...$(C_5MeH)SiMe_2(NHC_{12}H_{23})$.--.

Signed and Sealed this

Nineteenth Day of July, 1994

Attest:

BRUCE LEHMAN

Attesting Officer    Commissioner of Patents and Trademarks